United States Patent [19]

Dennis

[11] Patent Number: 5,334,520
[45] Date of Patent: Aug. 2, 1994

[54] PRODUCTION OF POLY-BETA-HYDROXYBUTYRATE IN TRANSFORMED ESCHERICHIA COLI

[75] Inventor: Douglas E. Dennis, Weyers Cave, Va.

[73] Assignee: Center for Innovative Technology, Herndon, Va.

[21] Appl. No.: 528,549

[22] Filed: May 25, 1990

[51] Int. Cl.$^5$ .................. C12P 7/40; C12N 1/20; C12N 1/38; C08G 63/06
[52] U.S. Cl. .................. 435/136; 435/142; 435/146; 435/252.33; 435/320.1; 528/361
[58] Field of Search .......... 435/252.3, 252.33, 320.1, 435/136, 243, 155, 280, 142, 146; 536/1.1, 124, 127, 26, 27, 28, 29; 528/361

[56] References Cited

U.S. PATENT DOCUMENTS

| | | |
|---|---|---|
| 2,811,511 | 10/1957 | Alderson . |
| 3,021,309 | 2/1962 | Cox et al. . |
| 3,036,959 | 3/1962 | Baptist . |
| 3,044,942 | 7/1962 | Baptist . |
| 3,107,172 | 10/1963 | Baptist et al. . |
| 3,121,669 | 2/1964 | Baptist .................. 435/146 |
| 3,275,610 | 9/1966 | Coty . |
| 3,293,225 | 12/1966 | Wakasa et al. . |
| 3,314,801 | 4/1967 | Cadmus et al. . |
| 3,406,114 | 10/1968 | Goren et al. . |
| 3,553,081 | 7/1971 | Goodhue et al. . |
| 3,579,549 | 5/1971 | Stockman et al. . |
| 3,624,047 | 11/1971 | Ogawa et al. . |
| 3,632,570 | 1/1972 | Gill . |
| 3,806,495 | 4/1974 | Schoen . |
| 3,923,782 | 12/1975 | Finn et al. . |
| 4,101,533 | 7/1978 | Lafferty et al. . |
| 4,138,291 | 2/1979 | Lafferty .................. 435/29 |
| 4,140,741 | 2/1979 | Lafferty et al. . |
| 4,211,846 | 7/1980 | Lafferty . |
| 4,237,224 | 12/1980 | Cohen et al. .................. 435/68 |
| 4,306,026 | 12/1981 | Maslen et al. . |
| 4,310,684 | 1/1982 | Vanlautem et al. . |
| 4,324,880 | 4/1982 | Dhein et al. . |
| 4,324,907 | 4/1982 | Senior et al. . |
| 4,326,035 | 4/1982 | Gabellieri . |
| 4,329,448 | 5/1982 | Cox et al. . |
| 4,336,334 | 6/1982 | Powell et al. .................. 435/146 |
| 4,337,181 | 6/1982 | Otey et al. . |
| 4,358,583 | 11/1982 | Walker et al. .................. 435/135 |
| 4,360,488 | 11/1982 | Barham et al. . |
| 4,365,088 | 12/1982 | Vanlautem et al. . |
| 4,385,026 | 5/1983 | Barham . |
| 4,391,766 | 7/1983 | Barham et al. . |
| 4,394,447 | 7/1983 | Cadmus et al. . |

(List continued on next page.)

FOREIGN PATENT DOCUMENTS

| | | |
|---|---|---|
| 0036699B2 | 9/1981 | European Pat. Off. . |
| 0046017A3 | 2/1982 | European Pat. Off. . |
| 0046344A3 | 2/1982 | European Pat. Off. . |

(List continued on next page.)

OTHER PUBLICATIONS

Ayres et al., Microbiology of Foods, W. M. Freeman & Company, San Francisco, 1980, pp. 191–192.
Byrom, Trends in Biotechnology 5:246–250 (1987).
Ploux, et al., The NADPH-Linked Acetoacetyl-COA
(List continued on next page.)

Primary Examiner—Stephanie W. Zitomer
Attorney, Agent, or Firm—Seed and Berry

[57] ABSTRACT

Methods are provided for enhancing the production of PHB from a transformed E. coli host which includes the genes coding for the PHB biosynthetic pathway. By inserting the genes coding for PHB into a host which includes a lactose utilization system, a low cost minimal medium including whey can be used as the fuel and carbon source for PHB production. A plasmid which codes for the PHB biosynthetic pathway plus four hundred extra bases on either side of the first and last genes in the pathway has been inserted into the host and has been shown to produce a larger amount of PHB accumulation in a shorter period of time than other plasmid constructs. $CaCl_2$ has been shown to be an effective agglomerating agent for agglomerating PHB which has been produced in a transformed E. coli host.

15 Claims, 6 Drawing Sheets

% PHB VS TIME

U.S. PATENT DOCUMENTS

| Number | Date | Name | Class |
|---|---|---|---|
| 4,396,763 | 8/1983 | Tsuchiya et al. | 536/1.1 |
| 4,427,614 | 1/1984 | Barham et al. | |
| 4,433,053 | 2/1984 | Hughes et al. | 435/141 |
| 4,477,654 | 10/1984 | Holmes et al. | 435/135 |
| 4,477,655 | 10/1984 | Holmes . | |
| 4,487,835 | 12/1984 | Uhlin et al. | |
| 4,491,575 | 1/1985 | Korsatko . | |
| 4,495,287 | 1/1985 | Uhlin et al. | |
| 4,499,189 | 2/1985 | Uhlin et al. | |
| 4,503,155 | 3/1985 | Miller et al. | |
| 4,508,823 | 4/1985 | Olsen . | |
| 4,529,797 | 7/1985 | Peik et al. | |
| 4,537,738 | 8/1985 | Holmes . | |
| 4,562,245 | 12/1985 | Stageman . | |
| 4,567,140 | 1/1986 | Voelskow et al. | |
| 4,575,551 | 3/1986 | Fujiyama et al. | |
| 4,599,311 | 7/1986 | Kawasaki . | |
| 4,603,070 | 7/1986 | Steel et al. | |
| 4,620,999 | 11/1986 | Holmes . | |
| 4,626,504 | 12/1986 | Puhler et al. | |
| 4,631,259 | 12/1986 | Clewell et al. | |
| 4,638,059 | 1/1987 | Sutherland . | |
| 4,647,657 | 3/1987 | Wan . | |
| 4,705,604 | 11/1987 | Vanlautem et al. | 435/146 |
| 4,711,848 | 12/1987 | Insley et al. | |
| 4,713,449 | 12/1987 | Vanderslice et al. | |
| 4,743,453 | 5/1988 | Ahern et al. | 435/141 |
| 4,752,580 | 6/1988 | Downs . | |
| 4,758,356 | 7/1988 | Downs . | |
| 4,760,022 | 7/1988 | Molin et al. | |
| 4,786,598 | 11/1988 | Lafferty et al. | 435/146 |
| 4,806,471 | 2/1989 | Molin et al. | |
| 4,806,482 | 2/1989 | Horowitz . | |
| 4,826,945 | 5/1989 | Cohn et al. | |
| 4,876,331 | 10/1989 | Doi . | |
| 4,900,299 | 2/1990 | Webb . | |
| 4,902,516 | 2/1990 | Korsatko et al. | |
| 4,910,145 | 3/1990 | Holmes et al. | |
| 4,948,733 | 8/1990 | Easson, Jr. et al. | |
| 4,950,749 | 8/1990 | Johal et al. | 536/127 |
| 4,952,496 | 8/1990 | Studier et al. | |
| 4,957,861 | 9/1990 | Lafferty et al. | |
| 4,960,866 | 10/1990 | Bendix et al. | |
| 4,965,197 | 10/1990 | Liebl et al. | |
| 4,968,611 | 11/1990 | Traussnig et al. | |
| 4,992,540 | 2/1991 | Jamas et al. | |
| 4,997,909 | 3/1991 | Doi . | |
| 5,004,664 | 4/1991 | Fuller et al. | |
| 5,008,108 | 4/1991 | Rha et al. | |
| 5,028,703 | 7/1991 | Jamas et al. | |
| 5,032,512 | 7/1991 | Witholt et al. | |
| 5,037,972 | 8/1991 | Jamas et al. | |
| 5,059,536 | 10/1991 | Page et al. | |
| 5,076,983 | 12/1991 | Loomis et al. | |
| 5,082,936 | 1/1992 | Jamas et al. | |
| 5,091,376 | 2/1992 | Easson, Jr. et al. | |
| 5,096,819 | 3/1992 | Page et al. | |
| 5,107,016 | 4/1992 | Pennetreau . | |
| 5,110,852 | 5/1992 | Gogolewski et al. | |
| 5,110,980 | 5/1992 | Ramsay et al. | |
| 5,124,371 | 6/1992 | Tokiwa et al. | |
| 5,126,255 | 6/1992 | Anderson et al. | |
| 5,135,859 | 8/1992 | Witholt et al. | |
| 5,138,029 | 8/1992 | Nishioka et al. | |

FOREIGN PATENT DOCUMENTS

| | | |
|---|---|---|
| 0052459B1 | 5/1982 | European Pat. Off. . |
| 0069497A2 | 1/1983 | European Pat. Off. . |
| 0078609B1 | 5/1983 | European Pat. Off. . |
| 0093021A2 | 11/1983 | European Pat. Off. . |
| 0104731B1 | 4/1984 | European Pat. Off. . |
| 0052460A1 | 5/1984 | European Pat. Off. . |
| 0108882A1 | 5/1984 | European Pat. Off. . |
| 0114086A2 | 7/1984 | European Pat. Off. . |
| 0144017A1 | 6/1985 | European Pat. Off. . |
| 0145233A2 | 6/1985 | European Pat. Off. . |
| 0149744B1 | 7/1985 | European Pat. Off. . |
| 0168095A1 | 1/1986 | European Pat. Off. . |
| 0204442A2 | 12/1986 | European Pat. Off. . |
| 0288908A2 | 2/1988 | European Pat. Off. . |
| 0285871A3 | 10/1988 | European Pat. Off. . |
| 0355307A2 | 2/1990 | European Pat. Off. . |
| 0431883A2 | 6/1991 | European Pat. Off. . |
| 0432443A1 | 6/1991 | European Pat. Off. . |
| 0435028A2 | 7/1991 | European Pat. Off. . |
| 0440165A2 | 8/1991 | European Pat. Off. . |
| 0466050A1 | 1/1992 | European Pat. Off. . |
| 0475785A2 | 3/1992 | European Pat. Off. . |
| 3937649A1 | 5/1991 | Fed. Rep. of Germany . |
| 4003827A1 | 8/1991 | Fed. Rep. of Germany . |
| 4036067A1 | 5/1992 | Fed. Rep. of Germany . |
| 229428A1 | 11/1985 | German Democratic Rep. . |
| 239609A1 | 10/1986 | German Democratic Rep. . |
| 276304A1 | 2/1990 | German Democratic Rep. . |
| 290914A5 | 6/1991 | German Democratic Rep. . |
| 294280A5 | 9/1991 | German Democratic Rep. . |
| 61-45778 | 9/1987 | Japan . |
| 63-198991 | 8/1988 | Japan . |
| 62-103228 | 11/1988 | Japan . |
| 1-27483 | 1/1989 | Japan . |
| 62-183260 | 1/1989 | Japan . |
| 62-204537 | 2/1989 | Japan . |
| 62-204538 | 2/1989 | Japan . |
| 62-224083 | 3/1989 | Japan . |
| 2-234683 | 3/1989 | Japan . |
| 63-49015 | 9/1989 | Japan . |
| 63-136748 | 12/1989 | Japan . |
| 1-304891 | 12/1989 | Japan . |
| 3-143397 | 6/1991 | Japan . |
| 3-216193 | 9/1991 | Japan . |
| 3-277628 | 12/1991 | Japan . |
| WO8607608 | 12/1986 | PCT Int'l Appl. . |

OTHER PUBLICATIONS

Reductase from *Zoogloea ramigera*, European J. Biochem., vol. 174, pp. 177–182, 1988.

Slater et al., *Am. Soc. for Microbiol.*, Annual Mtg., Abst. No. H-123, Mar. 1–6, 1987.

Johnson et al., *Virginia Journal of Science*, p. 150, May 19–22, 1987.

Slater et al., *Virginia Journal of Science*, p. 152, May 19–22, 1987.

WO89/00202–Peoples et al.

Reusch et al., "Poly-$\beta$-Hydroxybutyrate May Be Involved in Uptake of DNA in *Escherichia coli*", Federation of American Societies for Experimental Biology 72nd Annual Meeting; Abstract #8504, May 1–5, 1988.

Doi et al., "Hydrolytic Degradation of Microbial poly(hydroxyalkanoates)", Makromol. Chem. Rapid Commun., 10:227–230, May 1989.

Brandl et al., "Ability of the Phototrophic Bacterium *Rhodospirillum rubrum* to Produce Various Poly ($\beta$-Hydroxyalkanoates): Potential Sources for Biodegradable Polyesters", Int. J. Biol. Macromol., 11:49–55, Feb. 1989.

Arnold et al., "Synthesis of Stereoregular Poly(Alkyl Malolactonates)[a]", Makromol. Chem., Macromol. Symp. 6, 285–303, Dec. 1986.

Gross et al., "The Ring-Opening Polymerization of $\beta$-Butyrolactone to Synthesize Poly ($\beta$-Hydroxybuty-

OTHER PUBLICATIONS rate): A Mechanistic Study", Polym. Prepr. (Am. Chem. Soc., Div. Polym) (Chem.), 29:596–7, 1988.

Ballard et al., "Formation of Polymers of β-Hydroxybutyric Acid in Bacterial Cells and a Comparison of the Morphology of Growth with the Formation of Polyethylene in the Solid State", Recent Advances in Mechanistic and Synthetic Aspects of Polymerization, pp. 293–314, D. Reidel Publishing Company, 1987.

Fuller et al., "Cellular and Molecular Approaches to Polymer Synthesis by Bacteria", Massachusetts Univ., Amherst Dept. of Biochemistry, Journal vol. 08915; Annual Rept. Mar. 1, 1988–Feb. 22, 1989.

NERAC Inc., Copyright 1990; Oct. 3, 1990, pp. 1–18; "Tech Track Update: Bacteria-Produced Biopolymers".

Genetic Technology News, "Recombinant Bacteria Produce Polybetahydroxybutyrate Plastic", vol. 9, No. 9, Sep. 1989, p. 5.

Haywood et al., "Characterization of Two 3-Ketothiolases Possessing Differing Substrate Specificities in the Polyhydroxyalkanoate Synthesizing Organism *Alcaligenes eutrophus*", FEMS Microbiology Letters, 52:91–96, 1988.

Haywood et al., "The Role of NADH- and NADPH-Linked Acetoacetyl-CoA Reductases in the Poly-3-Hydroxybutyrate Synthesizing Organism *Alcaligenes Eutrophus*", FEMS Microbiology Letters, 52:259–264, 1988.

Reusch et al., "Poly-β-Hydroxybutyrate Membrane Structure and Its Relationship to Genetic Transformability in *Escherichia coli*", J. Bacteriol., 168:553–562, Nov. 1986.

Chemical Week, "A Versatile Polymer's Delayed Debut", Aug. 28, 1985.

Schubert et al., "Molecular Analysis of the *Alcaligenes Eutrophus* Poly(3-Hydroxybutyrate) Biosynthetic Operon: Identification of the N Terminus of Poly(3-Hydroxybutyrate) Synthase and Identification of the Promoter", J. Bacteriol., 173:168–175, Jan. 1991.

Peoples et al., "Poly-β-Hydroxybutyrate Biosynthesis in *Alcaligenes eutrophus* H16: Characterization of the Genes Encoding β-Ketothiolase and Acetoacetyl-CoA Reductase", J. Bio. Chem., 264:15293–15297, Sep. 1989.

Doi et al., "Biodegradation of Microbial Copolyesters: Poly(3-Hydroxybutyrate-co-3-hydroxyvalerate) and Poly (3-hydroxybutyrate-co-4-hydroxybutyrate)", Macromolecules, 23:26–31, 1990.

Computer Search-Miscellaneous Abstracts, pp. 1–60.

Steinbuchel et al., "Expression of the *Alcaligenes eutrophus* poly(β-hydroxybutyric acid)-Synthetic Pathway in *Pseudomas sp.*", Microbiol., 153:101–104, 1989.

Keeler, "Plastics Grown in Bacteria Inch Toward the Market", R & D Magazine, pp. 46–52, Jan. 1991.

Pool, "One Word, Son: Bugs", Discover, pp. 22–23, Jul. 1990.

Dawes, "Aspects of the Regulation of Polyhydroxyalkanoate Metabolism", International Symposium on Biodegradable Polymers, pp. 85–89, Oct. 29–31, 1990.

Fuller et al., "Biosynthesis and Biodegradation of Polyesters", International Symposium on Biodegradable Polymers, pp. 90–93; Oct. 29–31, 1990.

Doi, "Production and Biodegradation of Microbial Copolyesters", International Symposium on Biodegradable Polymers, pp. 94–98; Oct. 29–31, 1990.

Peoples et al., "Genes to PHA Polymers", International Symposium on Biodegradable Polymers, p. 108; Oct. 29–31, 1990.

Steinbuchel et al., "Molecular Analysis of Genes Essential for and Affecting the Synthesis of Poly (β-Hydroxyalkanoates) in *Alcaligenes eutrophus*", International Symposium on Biodegradable Polymers, pp. 109–113, Oct. 29–31, 1990.

Endo et al., "Preparation of Functional Poly(amino acid) and Their Application to Biodegradable Polymers", International Symposium on Biodegradable Polymers, pp. 114–118; Oct. 29–31, 1990.

Kalousek et al., "Release of Poly-β-Hydroxybutyrate Granules from *Escherichia coli* by Protein E-Mediated Lysis", International Symposium on Biodegradable Polymers, p. 150; Oct. 29–31, 1990.

Kawaguchi et al., "In Vivo $^{13}$C NMR Analysis of Poly(3-hydroxybutyrate) and Trehalose Metabolism in *Alcaligenes eutrophus*", International Symposium on Biodegradable Polymers, p. 151; Oct. 29–31, 1990.

Nakamura et al., "Biosynthesis of Biodegradable Copolyesters by *Alcaligenes eutrophus* from Various Carbon Substrates", International Symposium on Biodegradable Polymers, p. 152; Oct. 29–31, 1990.

Koyama et al., "One-Stage Production of P(3-Hydroxybutyrate-co-3-hydroxyvalerate) by *Alcaligenes eutrophus* in Fed Batch Culture", International Symposium on Biodegradable Polymers, p. 153; Oct. 29–31, 1990.

Liebergesell et al., "Cloning of the Genes for Poly(-β-Hydroxybutyric Acid) Synthesis of *Chromatium vinosum*", International Symposium on Biodegradable Polymers, p. 178, Oct. 29–31, 1990.

Hrabak, "Development of a New Production Process for PHB", International Symposium on Biodegradable Polymers, page unknown, Oct. 29–31, 1990.

Steinbuchel et al., "Genetic and Molecular Analysis of the *Alcaligenes eutrophus* Polyhydroxyalkanoate-Biosynthetic Genes and Accumulation of PHA in Recombinant Bacteria", Novel Biodegradable Microbial Polymers (E. A. Dawes, Ed.), pp. 143–159, 1990.

Witholt et al., "Bacterial Poly(3-Hydroxyalkanoates)", Novel Biodegradable Microbial Polymers ( E. A. Dawes, Ed.), pp. 161–173, 1990.

Huisman, "Metabolism of Poly(3-Hydroxyalkanoates) (PHAs) by *Pseudomonas oleovorans*", J. Bio. Chem., 266:2191–2198, Feb. 5, 1991.

Doi et al., "Biosynthesis and Characterization of Poly(-3-Hydroxybutyrate-co-4-Hydroxybutyrate) in *Alcaligenes eutrophus*", Int. J. Biol. Macromol., 12:106–111, Apr. 1990.

Capon et al., "Poly-3-Hydroxyalkanoates from Marine and Freshwater Cyanobacteria", Phytochemistry, 22:1181–1184, 1983.

Janes et al., "Molecular Characterization of the Poly-β-Hydroxybutyrate Biosynthetic Pathway of *Alcaligenes eutrophus* H16", Novel Biodegradable Microbial Polymers (E. A. Dawes, Ed.), pp. 175–190, 1990.

Smith et al., Principles of Biochemistry: General Aspects, McGraw-Hill, 1983, p. 53.

Sheeler et al., Cell and Molecular Biology, Third Edition, John Wiley & Sons, 1987, p. 284.

Studier et al., "Use of T7 RNA Polymerase to Direct Expression of Cloned Genes", Methods in Enzymology, 185:60–89, 1990.

Poirer et al., "Polyhydroxybutyrate, a Biodegradable Thermoplastic, Produced in Transgenic Plants", Science, 256:520–523, Apr. 24, 1992.

OTHER PUBLICATIONS

Peoples et al., "Poly-β-hydroxybutyrate (PHB) Biosynthesis in *Alcaligenes eutrophus* H16: Identification and Characterization of the PHB Polymerase Gene (phbC)", J. Bio. Chem., 264:15298–15303, Sep. 1989.

Findlay et al., "Polymeric Beta-Hydroxyalkanoates from Environmental Samples and *Bacillus megaterium*", Applied and Environ. Microbiol., 45:71–78, 1983.

Oldham et al., "Combined Determination of Poly-β-Hydroxyalkanoic and Cellular Fatty Acids in Starved Marine Bacteria and Sewage Sludge by Gas Chromatography with Flame Ionization or Mass Spectrometry Detection", Applied and Environ. Microbiol., 52:905–910, 1986.

Alfred Benzon, Inc., brochure, *Runaway Replication Plasmid Technology* (RAP ™).

Wallen et al., "Biopolymers of Activated Sludge", Environmental Science & Technology, 6:161–164, Feb. 2, 1972.

Wallen et al., "Poly-β-hydroxyalkanoate from Activated Sludge", Environmental Science & Technology, 8:576–579, Jun. 6, 1974.

Davis, "Cellular Lipids of a *Nocardia* Grown on Propane and n-Butane", Applied Microbiology, 12:301–304, Jul. 1964.

Marchessault et al., "Physical Properties of Poly-β-Hydroxyvalerate: a Natural Chiral Polyalkanoate", IUPAC "Macro Florence 1980: International Symposium on Macromoles preprints, 2:272–276, 1980.

Morikawa et al., "Pyrolysis of bacterial polyalkanoates", Canadian J. Chem., 59:2306–2313, 1981.

Ditta et al., "Broad host range DNA cloning system for Gram-negative bacteria: construction of a gene blank of *Rhizobium meliloti*", Proc. Natl. Acad. Sci., 77(12), 7347–7351, Dec. 1980.

Farrah et al., "Isolation of Exocellular Polymer from *Zoogloea* Strains MP6 and 106 and from Activated Sludge", Applied and Environ. Microbiol., 32(1), 33–37, Jul. 1976.

Ish-Horowicz, "Rapid and efficient cosmid cloning", Nucleic Acids Research, 9(13), 2989–2998, Jul. 10, 1981.

Okita et al., "Biosynthesis of Bacterial Glycogen", J. Biol. Chem., 256:6944–6952, 1981.

Parsons et al., "Production of Extracellular Polysaccharide Matrix by *Zoogloea ramigera*", Applied Microbiology, 21(4), 657–661, Apr. 1971.

Sinskey et al., "Biopolymers and Modified Polysaccharides", *Biotechnology in Food Processing*, 1986.

Stauffer et al., "Characterization of Zooglan-115, an Exocellular Glycan of *Zoogloea ramigera*-115", J. Food Sci., 45:746–952, 1980.

Norberg et al., "Production of Extracellular Polysaccharide by *Zoogloea ramigera*", Applied and Environ. Microbiol., 44:1231–1237, 1982.

Darzins et al., "Cloning of Genes Controlling Alginate Biosynthesis from a Mucoid Cystic Fibrosis Isolate of *Pseudomonas aeruginosa*", J. Bacteriol., vol. 159(1), pp. 9–18, 1984.

Cooper et al., "Production of Exopolysaccharides from Lactose by Wildtype *Zoogloea ramigera* and a Capsule Minus Mutant Strain Isolated by Buoyant Density Centrifugation", Abstract Production of Exopolysaccharides . . . , Dept. Chem., Eng., University of Wisconsin.

Okayama et al., "Bacteriophage Lambda Vector for Transducing a cDNA Clone Library into Mammalian Cells", Mol. and Cell., Biol., 5:1136–1142, 1985.

Computer Search of Ramigera and Gene.

Slater et al., "Cloning and Expression in Escherichia Coli of Alcaligenes Eutrophus H16 Poly-Beta-Hydroxybutyrate Biosynthetic Pathway" Oct., 1988, Journal of Bacteriology, pp. 4431–4436.

Schubert et al., "Cloning of the Alcaligenes Eutrophus Genes for Synthesis of Poly-Beta-Hydroxybutyric Acid (PHB) and Synthesis of PHB in Escherichia Coli," Dec., 1988, Journal of Bacteriology, vol. 170, No. 11, pp. 5837–5847.

Peoples et al., "BiosyntheticThiolase from Zoogloea ramigera: III. Isolation and characterization of the structural gene," Jan. 5, 1987, The Journal of BiologicalChemistry, vol. 262, No. 1, pp. 97–102.

Peoples et al., "Fine structural analysis of the Zooglea ramigera phbA–phbB locus encoding Beta-ketothiolase and acetoacetyl-CoA reductase: nucleotide sequence of phbB," Mar. 1989, Molecular Microbiology, vol. 3, #3, pp. 349–357.

PRODUCTION OF POLY-BETA-HYDROXYBUTYRATE IN TRANSFORMED ESCHERICHIA COLI

CROSS-REFERENCE TO RELATED APPLICATIONS

This patent application is related to the following co-pending patent application which is herein incorporated by reference:

"Cloning and Expression in *Escherichia coli* of the *Alcaligenes eutrophus* H16 Poly-Beta-Hydroxybutyrate Biosynthetic Pathway", of Douglas E. Dennis, which has Ser. No. 07/362,514 and was filed in the Patent and Trademark Office on Jun. 7, 1989.

BACKGROUND OF THE INVENTION

1. Field of the Invention

The present invention is generally related to the production of poly-beta-hydroxybutyrate (PHB) using *Escherichia coli* (*E. coli*) which has been genetically transformed by a vector carrying the genes coding for the PHB biosynthetic pathway and, more particularly, to the more efficient production of PHB in transformed *E. coli*.

2. Description of the Prior Art

PHB is an energy storage material produced by a variety of bacteria in response to environmental stress and is a homopolymer of D-(−)-3-hydroxybutyrate which has properties comparable to polypropylene. Because PHB is biodegradable, there is considerable interest in using PHB for packaging purposes as opposed to other plastic materials in order to reduce the environmental impact of human garbage. PHB also has utility in antibiotics, drug delivery, medical suture and bone replacement applications. PHB is commercially produced from *Alcaligenes eutrophus* (*A. eutrophus*) and sold under the tradename Biopol.

As described in the above incorporated patent application and in the article by Slater et al., "Cloning and Expression in *Escherichia coli* of the *Alcaligenes eutrophus* H16 Poly-β-Hydroxybutyrate Biosynthetic Pathway", *Journal of Bacteriology*, Vol. 170, No. 10, Oct. 1988, p. 4431–4436, which is also herein incorporated by reference, it was shown that *E. coli* could be genetically transformed with genes from *A. eutrophus* which code for the PHB biosynthetic pathway. *E. coli* are a far better vehicle for producing PHB than *A. eutrophus* since more is known about handling the bacteria, *E. coli*, i.e., *E. coli* is more easily controlled and manipulated. The transformed *E. coli* were able to express PHB in relatively large quantities.

Despite PHB's advantages over other materials, its high cost of production has hindered its performance in the market. Currently, PHB is produced in transformed *E. coli* by growing the *E. coli* on luria broth (LB) and using glucose as the carbon source. Approximately one third of the production cost of PHB is attributable to the cost of the rich LB medium and the glucose. If a less expensive carbon source could be utilized, the overall cost of PHB production could be significantly reduced. In addition, much of the total cost of PHB production is attributable to purifying the PHB produced in the *E. coli*. Currently, PHB is purified by centrifugation, followed by mechanical lysis of the cells to release PHB, a high temperature procedure to agglomerate the PHB, and finally a spray drying step to procure the purified granules. If a less expensive method were available for collecting the PHB from the *E. coli*, the overall cost of PHB production could be significantly reduced.

SUMMARY OF THE INVENTION

It is therefore an object of the present invention to provide improved techniques for producing PHB in transformed *E. coli*.

It is another object of this invention to provide a transformed *E. coli* strain which can accumulate PHB at higher levels than previous *E. coli* strains and which can utilize minimal medium containing whey for growing conditions.

It is yet another object of this invention to provide a method of agglomerating PHB granules from lysed *E. coli* cells using an ionic solution.

According to the invention, a strain of *E. coli*, i.e., *E. coli* HMS174, has been transformed by a vector containing a plasmid with the PHB biosynthetic pathway and approximately four hundred extra bases on both the upstream and downstream sides of the pathway. The HMS174 strain of *E. coli* was chosen because it contains a lactose utilization system and is recombination deficient so that a plasmid containing lactose genetic regions will not recombine and make the construct unstable. The lactose utilization system present in *E. coli* HMS174 has allowed whey to be used as a carbon source for the production of PHB. Whey is a waste product from cheese processing and is very inexpensive. Experiments have been performed which show that the strain of transformed *E. coli* grows in minimal medium containing whey and has an average yield of PHB of approximately 85% (PHB dry weight/total cell dry weight).

In addition, experiments have been conducted which show that PHB produced in transformed *E. coli* may be agglomerated with various ionic solutions. To retrieve purified PHB in large quantities, the transformed *E. coli* cells are first lysed by mechanical or physical means, such as by sonication, or by genetic means. Then, the cells are incubated in an ionic solution, such as 10 millimolar (mM) calcium chloride ($CaCl_2$), which agglomerates the PHB granules. Finally, the agglomerates are centrifuged from the culture at low speed. Experiments show that nearly all (100%) of the PHB in the culture is agglomerated and recovered by this process. The results are especially exciting since the same type of agglomeration is not possible for retrieving PHB from *A. eutrophus*.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF A PREFERRED EMBODIMENT OF THE INVENTION

Figure 1:
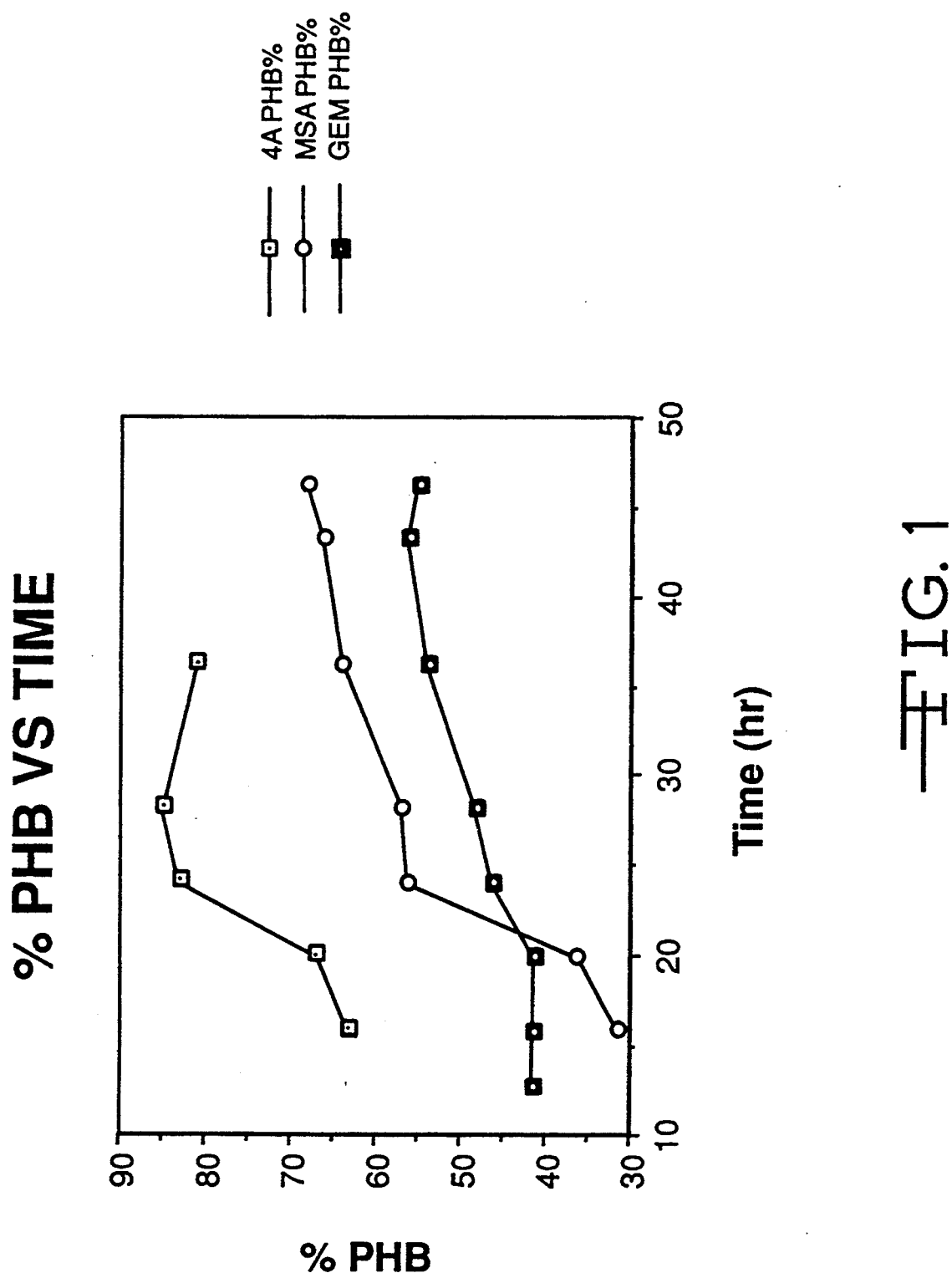
FIG. 1 is a line graph showing PHB accumulation versus time for a variety of *E. coli* clones containing different plasmid constructs.

Referring now to the drawings, and more particularly to FIG. 1, it is shown that the *E. coli* strain HMS174 containing the plasmid p4A accumulates a greater percentage of PHB in a shorter period of time than other *E. coli* clones containing different plasmid constructs. The *E. coli* strain HMS174 is available from the Yale *E. coli* Stock Center, Dept. of Biology, 355 OML, Yale University, P.O. Box 6666, New Haven, Conn. 06511-7444, Barbara Bachman curator. The p4A plasmid carries the PHB biosynthetic pathway and approximately four hundred extra bases to the upstream and downstream sides of the PHB biosynthetic pathway on the vector pTZ-18U. The vector pTZ-18U is available from United States Biochemicals. MSA carries the PHB biosynthetic pathway on the vector pTZ-18U and the E-lysis gene from phage phi X 174 on another compatible plasmid. MSA differs from p4A in that it has approximately four hundred extra bases on the upstream side of the PHB biosynthetic pathway (i.e., the PHB biosynthetic pathway is cloned into pTZ-18U to create pTZ-18U–PHB called "MSA", and p4A is pTZ-18U-PHB less four hundred bases on the upstream side of the PHB biosynthetic pathway). GEM carries the PHB biosynthetic pathway on the vector pGEM-7F+ which is available from the Promega Corporation.

The p4A, pTZ-18U–PHB (MSA), and pGEM7f-PHB(GEM) clones were all constructed from the *E. coli* clone harboring the PHB biosynthetic pathway discussed in the above-referenced and incorporated co-pending patent application and journal article using conventional molecular cloning techniques. As was disclosed in the patent application and journal article, the PHB biosynthetic pathway can be isolated from *A. eutrophus* and expressed in *E. coli*. The PHB biosynthetic pathway is approximately five kilobases in length and contains bases coding for β-ketothiolase, NADP-linked acetoacetyl-coenzyme A (CoA) reductase, and PHB synthetase. FIG. 1 shows that the MSA and GEM clones do not produce as much PHB as the p4A clone.

*E. coli* HMS174 was chosen as the host because it contains a lactose utilization system and it is recombination deficient. Recombination deficiency assures that a plasmid containing lactose genetic regions will not recombine and make the construct unstable. As will be described below, the presence of the lactose utilization system in HMS174 allows whey, a cheese manufacturing waste product whose major component is lactose, to be used as the carbon source for PHB production. In making the transformed *E. coli* strain, the plasmid p4A, which is the PHB biosynthetic pathway plus four hundred bases upstream and downstream of the PHB biosynthetic pathway cloned into the United States Biochemical vector pTZ-18U, is electroplated into the *E. coli* HMS174. A strain of the *E. coli* harboring the p4A plasmid has been deposited with the American Type Culture Collection of 12301 Parklawn Drive, Rockville, Md. on May 23, 1990, and bears deposit number: 68329 designated as *E. coli* HMS174/p4A (PHB 90) and deposited in accordance with the requirements of the Budapest Treaty.

Experiments were performed which showed that the HMS174 strain of *E. coli* which had been transformed with the p4A plasmid could be grown on minimal medium containing whey. The minimal medium used was M9 minimal medium which is described in most microbiological biology texts. Table 1 lists the formulation for a 5X concentrate of M9 minimal medium where each of the listed components is added to a liter flask and water is added to one liter.

TABLE 1

5X M9 MINIMAL MEDIUM FORMULATION

| |
|---|
| 30 g $Na_2HPO_4$ |
| 15 g $KH_2PO_4$ |
| 5 g $NH_4Cl$ |
| 2.5 g NaCl |

Whey was purchased from Sigma chemicals as a powder of bovine whey, and was made by stirring 20 grams of whey in water that had a final volume of 100 ml. Stirring took place with mild heating for approximately 30 minutes. This solution was then autoclaved and particulates that precipitated during centrifugation were pelleted by centrifugation at 10,000×g for 10 min. The remaining supernate was used as the whey carbon source.

In the experiments, the HMS174 *E. coli* strain containing the plasmid p4A was inoculated from a plate culture into 50 ml of M9 minimal medium+whey solution. Table 2 lists the formulation for 50 ml of minimal medium containing whey at a final concentration of 8%.

TABLE 2

MINIMAL MEDIUM + WHEY FOR PHB PRODUCTION

| | |
|---|---|
| 10 ml | 5X M9 medium |
| 20 ml | $ddH_2O$ (double distilled water) |
| 50 μl | 1 M $MgSO_4$ |
| 5 μl | 0.5% Thiamine |
| 250 μl | 20% casamino acids |
| 20 ml | 20% whey solution |

The inoculated culture was grown at 37° C. for 48 hours in an orbital incubator shaker at 300 rpm in a 250 ml baffled flask. After the 48 hour incubation time, the culture was stopped and the cells were harvested. Gas chromatography was used to analyze the PHB content.

Figure 2A:
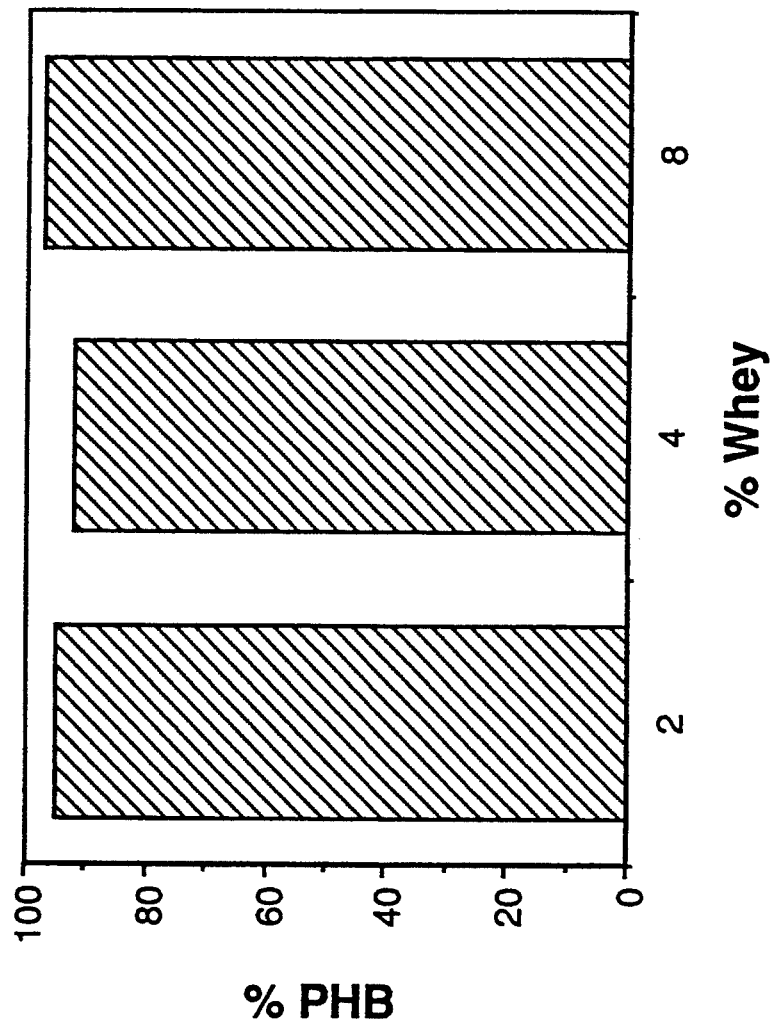
FIGS. 2a and 2b are bar graphs showing the accumulation of PHB produced by transformed *E. coli* using minimal medium and whey.
Figure 2B:
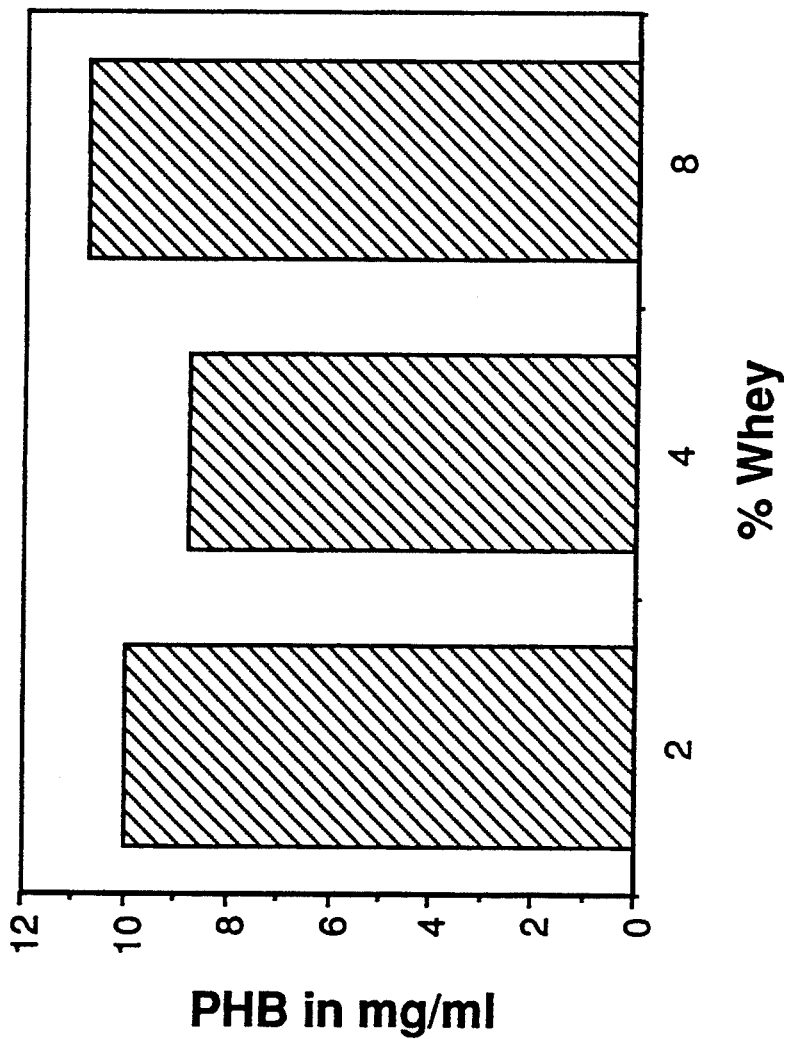

FIGS. 2a and 2b respectively show the percentage of PHB accumulated in the cells, expressed as PHB weight per cell divided by the total weight of the cell, and the yield of PHB in the cells, expressed as the total PHB made in mg/ml, for differing concentrations of whey in solution with the minimal medium. FIGS. 2a and 2b show that even with very low concentrations of whey, i.e., 2% in solution, high concentrations of PHB accumulation (i.e., greater than 90%) and high yields of PHB (i.e., approximately 10 mg/ml). While FIGS. 2a and 2b show that medium with higher concentrations of whey tended to produce greater concentrations and yields of PHB, it was noted that after the whey concentration exceeds 8%, PHB production begins to fall.

In the above experiments, PHB production was analyzed after forty eight hours of incubation; however, it should be noted that significant PHB production was observed after twenty four hours of incubation. In addition, it is anticipated that the relative concentrations of the $Na_2HPO_4$, $KH_2PO_4$, $NH_4Cl$, and NaCl in the 5X minimal medium formulation and the relative concentrations of the 5X minimal medium, double distilled water, $MgSO_4$, Thiamine, casamino acids, and whey solution could be varied while still allowing production of PHB in a transformed *E. coli* host having a lactose utilization system.

Utilizing whey as the carbon source for the production of PHB, where the whey is present in minimal medium, is expected to result in considerable cost savings over the prior art practice of using rich medium with glucose for producing PHB. The prior art transformed *E. coli* cells which had plasmids coding for the PHB biosynthetic pathway, which were discussed in the co-pending patent application and journal article, could not be grown using whey as the carbon source since those bacteria did not have a lactose utilization system present therein. PHB cannot be produced using whey as its carbon source in the native host, *Alcaligenes eutrophus*, because that bacteria also lacks a lactose utilization system. In addition, as shown in FIG. 1, transforming a particular *E. coli* host, HMS174, with a particular plasmid, p4A, allows the production of PHB at much higher percentages than when the *E. coli* is transformed with a different vector which also codes for the PHB biosynthetic pathway.

Because the PHB is being produced in *E. coli*, rather than its native host (*A. eutrophus*), the applicant believed that the PHB polymer produced by the transformed *E. coli* might have different physical properties from PHB produced in *A. eutrophus*. In particular, the applicant conducted experiments to determine if PHB produced by a transformed *E. coli* could be agglomerated by various ionic solutions. In the experiments, PHB was produced in transformed *E. coli* as discussed in the above-incorporated co-pending patent application and journal article. Briefly, a PHB-producing strain is grown in Luria broth (LB) containing 1% glucose for 24 hours at 37° C. in a shake flask culture. The cells are pelleted by centrifugation (2,000×g for 5 min) and then resuspended in a volume of water equal to the original culture. The cells were then lysed by sonication and various ionic reagents were added to the solution. Table 3 shows the aggregative effect on PHB produced in transformed *E. coli* by various ionic solutions.

TABLE 3

| AGGREGATION OF PHB BY VARIOUS IONIC SOLUTIONS | |
|---|---|
| Solution* | Degree of Aggregation** |
| $KH_2PO_4$ | ++ |
| NaCl | + |
| CsCl | − |
| $MgSO_4$ | +++ |
| $K_2HPO_4$ | + |
| $MgCl_2$ | ++++ |
| $(NH_4)_2HPO_4$ | + |
| MgOAc | ++++ |
| NaOAc | ++ |
| KCl | − |
| KOAc | − |
| $CaCl_2$ | ++++ |
| $(NH_4)OAc$ | − |

*All solutions were at a final concentration of 1M.
**Agglomeration was subjectively graded using micrographs of each aggregate. "++++" signifies the best agglomeration and "+" signifies the lowest amount of agglomeration. "−" signifies no agglomeration.

Table 3 shows that several ionic solutions cause PHB produced in transformed *E. coli* to agglomerate. The best agglomerating agent was $CaCl_2$ based on a subjective judgement concerning the speed and size of the agglomerates. The agglomeration effect of $CaCl_2$ on PHB produced in transformed *E. coli* is especially interesting since $CaCl_2$ does not cause PHB produced in its native *A. eutrophus* to agglomerate (i.e., an experiment was performed where PHB granules were obtained from lysed *Alcaligenes* H16 *eutrophus* and subjected to calcium chloride wherein no agglomeration was observed).

Experiments were conducted to determine the ideal concentration of $CaCl_2$ to use for agglomerating PHB. In the experiments, the transformed *E. coli* cells were prepared and lysed as described above, then the solutions were brought to different mM $CaCl_2$ concentrations using a 1M stock $CaCl_2$ solution. With low concentrations of $CaCl_2$, e.g., 1 mM, very long incubation times were required for PHB granules to agglomerate and only small agglomerates were produced. With high concentrations of $CaCl_2$, e.g., 100 mM and above, agglomeration occurred almost instantaneously and resulted in large "snowflake"-like particles that fell to the bottom of the tube. However, the agglomerates achieved with high concentrations of $CaCl_2$ appeared to have large amounts of cell debris. Therefore, high concentrations of $CaCl_2$ are not desirable for agglomeration. When medium concentrations of $CaCl_2$ were used, e.g., 5 mM to 30 mM, agglomeration of medium sized pellets occurred within a short incubation period of 5 to 15 minutes. Use of 10 mM $CaCl_2$ was determined to produce the best agglomeration results in terms of speed and size of agglomerate formation.

Experiments were performed to determine the percentage of PHB agglomerated by $CaCl_2$ versus the percentage of PHB left in solution. In the experiments, a PHB-producing strain of *E. coli* was grown in Luria broth containing 1% radio labelled glucose for 24 hours at 37° C. in a shake flask culture. The cells were pelleted by centrifugation (2,000×g for 5 min) and then resuspended in a volume of water equal to the original culture. The cells were then lysed by sonication and then the solution was brought to 10 mM by the addition of a 1M calcium chloride stock. The tube was incubated 10 min at room temperature and then centrifuged at 400×g for 2 min. The agglomerated PHB granules pelleted, while much of the cell debris stayed in the supernate. The supernatant was then aspirated. To determine the distribution of PHB in the pellet and supernatant, the pellet and supernatant were measured using either capillary gas chromatography or liquid scintillation counting.

Figure 3:
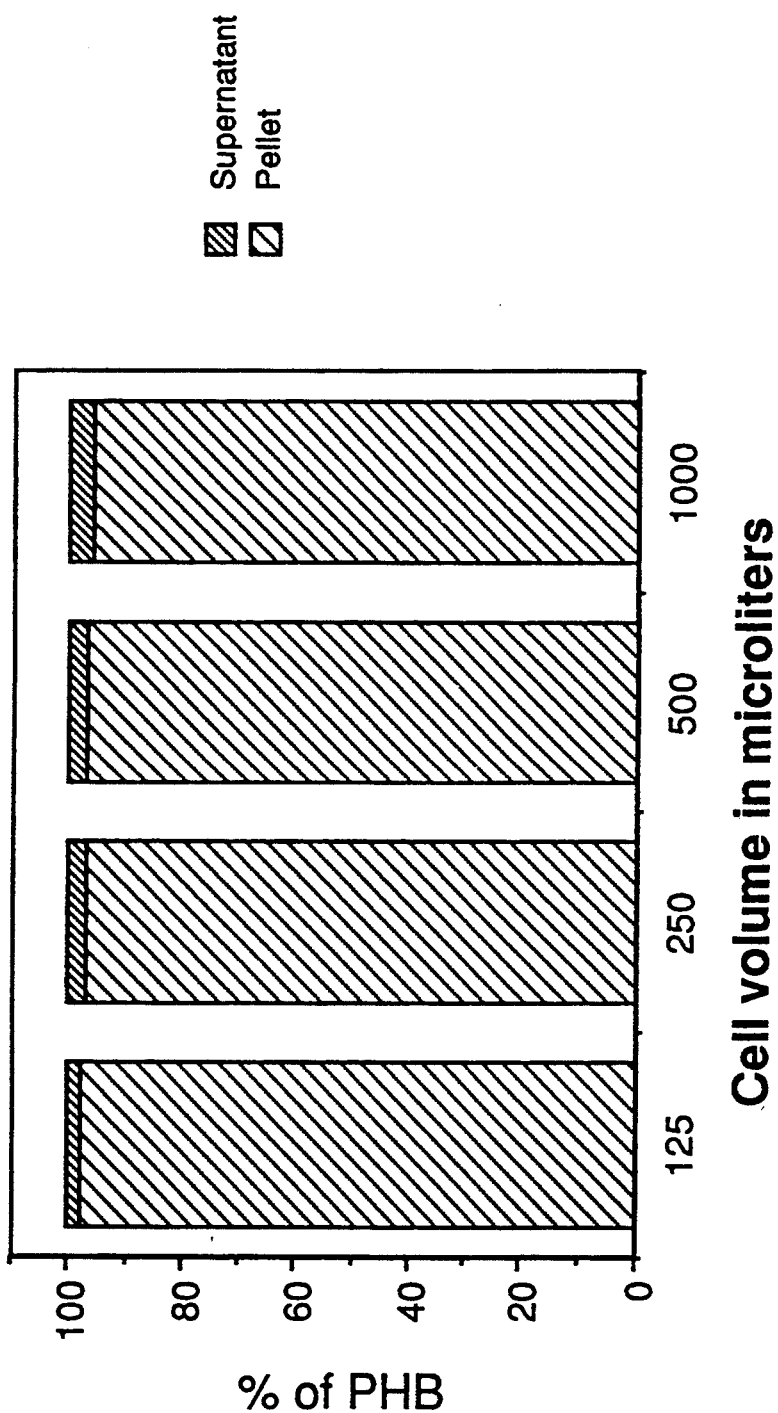
FIG. 3 is a bar graph showing the percentage of PHB agglomeration using $CaCl_2$.

FIG. 3 shows that nearly all (100%) of the PHB in the culture was agglomerated and recovered by the above process. In this experiment, the amount of PHB was measured only by gas capillary chromatography. This experiment was done at several cell volumes to determine if the volume of the flask influenced the degree of agglomeration and it was found that in all volumes nearly all of the PHB was agglomerated and subsequently pelleted by centrifugation.

Figure 4:
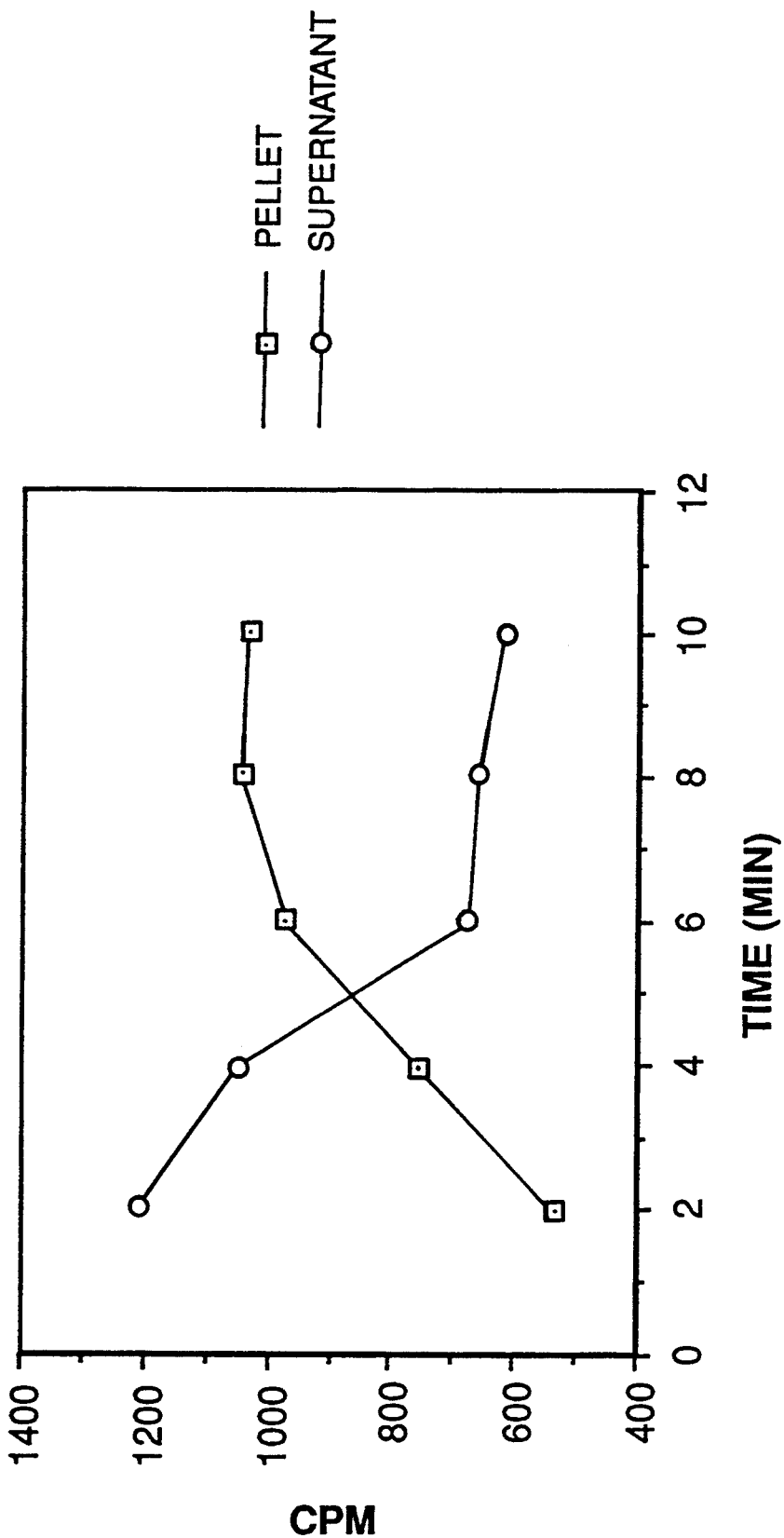
FIG. 4 is a line graph showing the PHB agglomerations versus time where PHB is accumulated in the presence of radiolabelled glucose and then subjected to the agglomeration procedure.

FIG. 4 shows that it is extremely important that the culture be allowed sufficient time for agglomeration to occur, otherwise the yield is reduced. Rather than allowing a full ten minute incubation time after the solution was adjusted to 10 mM $CaCl_2$, the pellet and supernatant fractions were counted at two minute timed intervals after the adjustment. FIG. 4 shows that during the first few minutes after adding $CaCl_2$ the amount of PHB present in the supernatant is actually greater than in the pellet. However, after eight minutes (where the amount of PHB measured in the pellet begins to level off), the amount of PHB in the pellet is far greater than in the supernatant fraction. It should be noted at this point that this experiment measures radioactive $^{14}$Carbon, most of which is incorporated into PHB as $^{14}$C-glucose (approximately 60% is incorporated), but some of which is present as soluble material. Therefore, even though nearly all of the PHB is precipitated, there is still a large number of counts in the superhate that is due to the soluble radioactive glucose.

Figure 5:
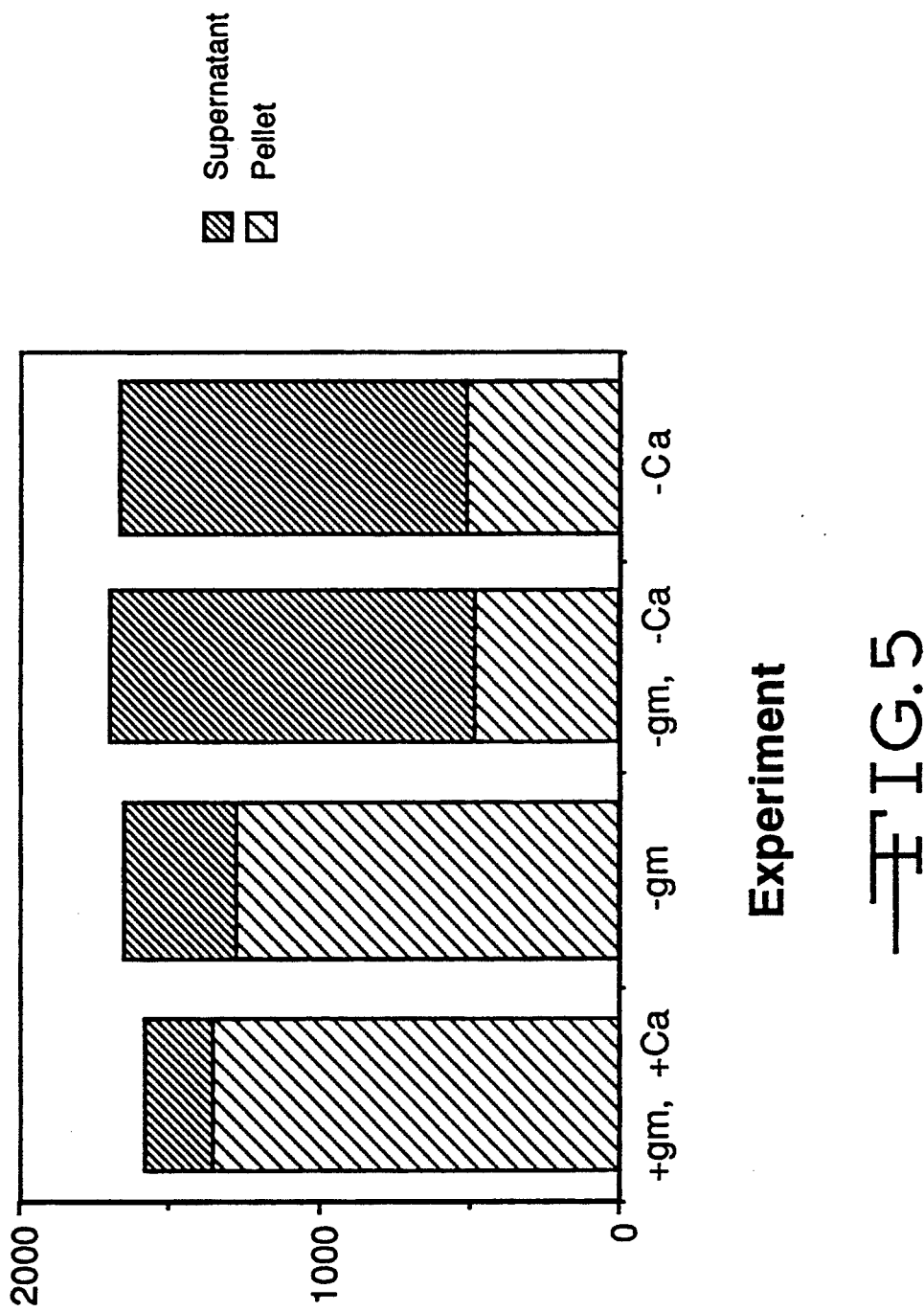
FIG. 5 is a bar graph showing the contrasting effects of glass milk and calcium on PHB agglomeration.

FIG. 5 shows that agglomeration of PHB can be enhanced by the addition of nucleating agents such as glass milk available from Bio 101. In FIG. 5, the counts per minute (CPM) of the pellet and supernatant fractions are displayed where "+gm, +Ca" indicates PHB agglomeration in the presence of glass milk and 10 mM CaCl$_2$, "−gm" indicates PHB agglomeration in the presence of 10 mM CaCl$_2$ without glass milk, "−gm, −Ca" indicates PHB agglomeration in the absence of glass milk and CaCl$_2$, and "−Ca" indicates PHB agglomeration in the presence of glass milk and in the absence of CaCl$_2$. From FIG. 5, it can be seen that the enhancement of agglomeration by the addition of nucleating agents is not very large; therefore, larger production schemes may not be greatly benefitted by the use of such agents.

While the invention has been described in terms of its preferred embodiments where a strain of transformed *E. coli* has been created which can accumulate larger quantities of PHB while using an inexpensive carbon source such as whey for PHB production and an ionic solution such as CaCl$_2$ can be used to agglomerate PHB, those skilled in the art will recognize that the invention can be practiced with modification within the spirit and scope of the appended claims.

Having thus described my invention, what I claim as new and desire to secure by Letters Patent is as follows:

1. An *Escherichia coli* bacterial host transformed by a vector consisting essentially of a deoxyribonucleic acid sequence encoding the poly-beta-hydroxybutyrate biosynthetic pathway of *Alcaligenes eutrophus* wherein the bacterial host has a lactose utilization system and grows in minimal medium containing whey and wherein the bacterial host is *Escherichia coli* strain ATCC 68329.

2. A method for producing poly-beta-hydroxybutyrate, comprising the steps of:
   providing a culture of the bacterial host of claim 1;
   growing said culture in a growth medium comprising minimal medium and whey for a period greater than twenty four hours, said bacterial host producing intra-cellular poly-beta-hydroxybutyrate;
   lysing said bacterial host in said culture to release said poly-betahydroxybutyrate; and
   collecting said poly-beta-hydroxybutyrate.

3. The method as recited in claim 2 in which said *Escherichia coli* bacterial host is grown in a growth medium comprising:
   0.6% Na$_2$HPO$_4$;
   0.3% KH$_2$PO$_4$;
   0.1% ammonium chloride;
   0.05% sodium chloride;
   58.84% water;
   0.012% magnesium sulfate;
   0.0005% thiamine;
   0.01% casamino acids; and,
   40% whey solution.

4. The method as recited in claim 2 wherein said minimal medium is approximately twenty percent of said growth medium, said whey is approximately forty percent of said growth medium, and water is approximately forty percent of said growth medium.

5. A method as recited in claim 2 wherein said step of collecting includes the step of exposing said released poly-beta-hydroxybutyrate to an ionic reagent selected from the group consisting of magnesium sulfate, magnesium chloride, magnesium acetate, and calcium chloride, said ionic reagent being of sufficient concentration to agglomerate said poly-beta-hydroxybutyrate.

6. A method as recited in claim 5 wherein said ionic reagent is calcium chloride at a concentration ranging between one molar and one millimolar.

7. A method as recited in claim 6 wherein said calcium chloride has a concentration of approximately ten millimolar.

8. A method for agglomerating poly-beta-hydroxybutyrate which has been intracellularly produced in a culture of *Escherichia coli* (strain ATCC 68329) bacterial host which has been transformed by a vector the vector containing a deoxyribonucleic acid sequence coding for the poly-beta-hydroxybutyrate biosynthetic pathway from *Alcaligenes eutrophus*, comprising the steps of:
   lysing said bacterial hosts to release said poly-beta-hydroxybutyrate; and
   adding to said released poly-beta-hydroxybutyrate a sufficient quantity of an ionic reagent selected from the group consisting of magnesium sulfate, magnesium chloride, magnesium acetate and calcium chloride, said sufficient quantity of said ionic reagent agglomerating granules of said poly-beta-hydroxybutyrate.

9. A method as recited in claim 8 wherein said ionic reagent is calcium chloride.

10. A method as recited in claim 8 wherein said calcium chloride is present at a concentration ranging between one molar and one millimolar.

11. A method as recited in claim 10 wherein said calcium chloride is present at a concentration of approximately 10 mM.

12. A plasmid designated as p4A and deposited with the American Type Culture Collection in *Escherichia coli* strain HMS 174 under accession number 68329.

13. The method recited in claim 8 further comprising the step of adding a nucleating agent to said quantity of said ionic reagent.

14. A method as recited in claim 10 wherein said calcium chloride is present at a concentration ranging from about 5 mM to about 30 mM.

15. A plasmid designated as pTZ-18U PHB and deposited with the American Type Culture Collection in *Escherichia coli* strain HMS174 under accession number 69064.

* * * * *